United States Patent [19]

Guaciaro et al.

[11] Patent Number: 5,438,035

[45] Date of Patent: Aug. 1, 1995

[54] METHODS FOR CONTROLLING UNDESIRABLE PLANT SPECIES WITH BENZODIAZEPINE COMPOUNDS

[75] Inventors: Michael A. Guaciaro, Hightstown; Philip M. Harrington, Cranbury; Gary M. Karp, Princeton Junction, all of N.J.

[73] Assignee: American Cyanamid Company, Wayne, N.J.

[21] Appl. No.: 265,478

[22] Filed: Jun. 24, 1994

[51] Int. Cl.$^6$ .......................................... A01N 43/48
[52] U.S. Cl. .................... 504/191; 504/220; 504/219; 540/506
[58] Field of Search ............... 504/219, 220, 191

[56] References Cited

U.S. PATENT DOCUMENTS

| | | | |
|---|---|---|---|
| 3,646,055 | 2/1972 | Hester | 260/308 C |
| 3,681,341 | 8/1972 | Earley | 260/239.3 D |
| 3,717,654 | 2/1973 | Hester | 260/308 C |
| 3,947,408 | 3/1976 | Wright, Jr. | 260/239.3 T |
| 3,985,732 | 10/1976 | Wright, Jr. | 260/239.3 T |
| 4,031,079 | 6/1977 | Mohrbacher et al. | 260/239.3 D |
| 4,185,016 | 1/1980 | Takanabe et al. | 260/239.3 T |
| 4,316,839 | 2/1982 | Gerecke et al. | 260/239.3 T |
| 4,352,815 | 10/1982 | Hunkeler et al. | 424/273 R |
| 4,352,817 | 10/1982 | Hunkeler et al. | 424/273 R |
| 4,772,599 | 9/1988 | Wätjen | 514/220 |
| 5,114,462 | 5/1992 | Moser et al. | 71/88 |

OTHER PUBLICATIONS

CA 108:150504. Suesse et al (DD 249476) 1986.
CA 108:131865. Suesse et al (DD 249475) 1986.
W. B. Wright, Jr. et al, Journal of Medicinal Chemistry, 21, pp. 1087–1089 (1978).
P. J. McCloskey and A. G. Schultz, Journal of Organic Chemistry, 53, pp. 1380–1383 (1988).
Tita and M. J. Kornet, Journal of heterocyclic Chemistry, 24, pp. 409–413 (1987).
M. Mori, et al, Tetrahedron, 42, pp. 3793–3806 (1986).
T. Nagasaka, et al, Tetrahedron Letters, 30, pp. 1871–1872 (1989).
A. G. Schultz, et al, Journal of the American Chemical Society, 109, pp. 6493–6502 (1987).
E. Wolf and H. Kohl, Liebigs Ann. Chem., pp. 1245–1251 (1975).
A. Kamal, Journal of Organic Chemistry, 56, pp. 2237–2240 (1991).
R. Singh, et al, Indian Journal of Chemistry, 20B, pp. 129–131 (1981).
A. E. Azzouny, et al, Pharmazie, 32, pp. 318–323 (1977).

*Primary Examiner*—S. Mark Clardy
*Attorney, Agent, or Firm*—Gregory M. Hill

[57] ABSTRACT

There are provided methods for controlling undesirable plant species with benzodiazepine compounds of formulas I and II

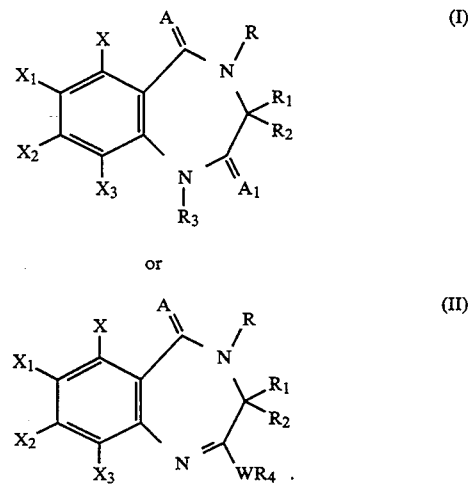

Further provided are herbicidal compositions comprising those compounds.

15 Claims, No Drawings

METHODS FOR CONTROLLING UNDESIRABLE PLANT SPECIES WITH BENZODIAZEPINE COMPOUNDS

BACKGROUND OF THE INVENTION

Weeds cause tremendous global economic losses by reducing crop yields and lowering crop quality. In the United States alone, agronomic crops must compete with hundreds of weed species. Moreover, some crop damage due to inadvertent overexposure to certain herbicides used to control undesirable plant species has occurred.

Accordingly, there is ongoing research to discover and develop more effective herbicidal agents for the selective control of weeds in the presence of crops. If successful, inadvertent overexposure to such agents will cause less crop damage, and perhaps eliminate such damage altogether.

Certain benzodiazepine compounds are known to possess antianxiety, antibiotic, blood pressure-lowering, respiratory-depressing, antiataxia and/or anticonvulsant activity (see, e.g., U.S. Pat. Nos. 3,681,341, 3,947,408, 3,985,732, 4,031,079, 4,185,016, 4,316,839, 4,352,815, 4,352,817 and 4,772,599; W. B. Wright, Jr., et al, Journal of Medicinal Chemistry, 21, pp. 1087–1089 (1978); P. J. McCloskey and A. G. Schultz, Journal of Organic Chemistry, 53, pp. 1380–1383 (1988); T. T. Tita and M. J. Kornet, Journal of Heterocyclic Chemistry, 24, pp. 409–413 (1987); M. Mori, et al, Tetrahedron, 42, pp. 3793–3806 (1986); T. Nagasaka, et al, Tetrahedron Letters, 30, pp. 1871–1872 (1989); A. G. Schultz, et al, Journal of the American Chemical Society, 109, pp. 6493–6502 (1987); E. Wolf and H. Kohl, Liebigs Ann. Chem., pp. 1245–1251 (1975); A. Kamal, Journal of Organic Chemistry, 56, pp. 2237–2240 (1991); R. Singh, et al, Indian Journal of Chemistry, 20B, pp. 129–131 (1981); and A. E. Azzouny, et al, Pharmazie, 32, pp. 318–323 (1977)).

However, no herbicidal utility for the benzodiazepine compounds is disclosed or suggested in those patents and publications.

It is an object of the present invention to provide a method for controlling undesirable plant species with benzodiazepine compounds.

It is also an object of the present invention to provide a method for the selective control of undesirable plant species growing in the presence of cereal crops using those compounds.

It is yet another object of the present invention to provide herbicidal compositions containing those benzodiazepine compouns. These and other objects of the present invention will become more apparent from the detailed description thereof set forth below.

SUMMARY OF THE INVENTION

The present invention provides a method for controlling undesirable plant species which comprises applying to the foliage of said plants or to the soil, water or other medium water containing seeds or other propagating organs there-of, a herbicidally effective amount of a benzodiazepine compound having the structural formula

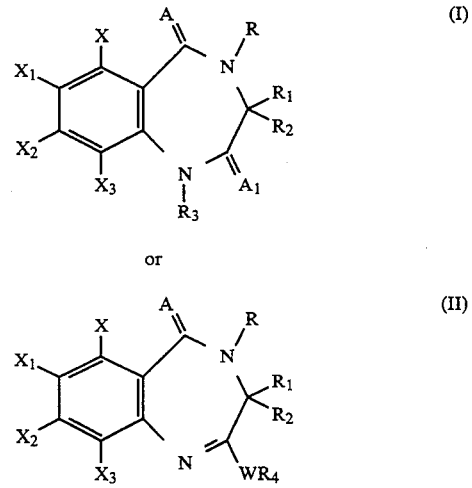

wherein

X is hydrogen, halogen, $C_1$–$C_4$haloalkyl, $C_1$–$C_4$alkoxy, $C_1$–$C_4$haloalkoxy, $C_2$–$C_3$alkenyl, $C_2$–$C_3$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$X_1$ is hydrogen, halogen, methyl, $C_1$–$C_4$haloalkyl, $C_1$–$C_4$alkoxy, $C_1$–$C_4$haloalkoxy, $C_2$–$C_5$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy group;

$X_2$ is hydrogen, $C_1$–$C_4$alkyl, $C_1$–$C_4$alkoxy, $C_1$–$C_4$haloalkoxy, $C_2$–$C_3$alkenyl, $C_2$–$C_3$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$X_3$ is hydrogen, $C_1$–$C_4$alkyl, $C_1$–$C_4$haloalkyl, $C_1$–$C_4$haloalkoxy, $C_2$–$C_3$alkenyl, $C_2$–$C_3$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_5$ is hydrogen, $C_1$–$C_4$alkyl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or an alkali metal, alkaline earth metal, manganese, copper, zinc, cobalt, silver, nickel, ammonium or organic ammonium cation;

$R_6$ and $R_7$ are each independently $C_1$–$C_4$alkyl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or $R_6$ and $R_7$ are taken together to form a ring in which $R_6R_7$ is represented by —$(CH_2)_n$— where n is an integer of 2, 3, 4 or 5;

m is an integer of 0, 1 or 2;

$R_8$ is hydrogen, $C_1$–$C_4$alkyl, $C_1$–$C_4$haloalkyl, $NR_{10}R_{11}$, $OR_{12}$ or phenyl optionally substituted with one or more halogen, nitro, cyano, $C_1$–$C_4$alkyl, $C_1$-$C_4$haloalkyl, $C_1$-$C_4$alkoxy or $C_1$-$C_4$haloalkoxy groups;

$R_{10}$ and $R_{11}$ are each independently hydrogen, $C_1$-$C_4$alkyl, benzyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, phenyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, or $R_{10}$ and $R_{11}$ are taken together to form a ring in which $R_{10}R_{11}$ is represented by —$(CH_2)_q$— where q is an integer of 2, 3, 4 or 5;

$R_{12}$ is hydrogen or $C_1$-$C_4$alkyl;

$R_9$ is hydrogen, $C_1$-$C_4$alkyl or phenyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups;

A, $A_1$ and W are each independently O or S with the proviso that when $A_1$ is S then A is O;

R is $C_3$-$C_6$cycloalkyl, $C_2$-$C_5$alkenyl, $C_2$-$C_5$alkynyl, $C_1$-$C_5$alkyl optionally substituted with one $CO_2R_{13}$ group, one phenyl group optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, or one 5- or 6-membered heterocycle group containing one to three nitrogen atoms, one oxygen atom and/or one sulfur atom and two to five carbon atoms optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, phenyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups with the proviso that the para-position of the phenyl ring is not substituted, a 5- or 6-membered heterocycle group containing one to three nitrogen atoms, one oxygen atom and/or one sulfur atom and two to five carbon atoms optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, or R may be taken together with $R_1$ and the atoms to which they are attached to form a five membered saturated ring substituted with one to three $C_1$-$C_4$alkyl groups;

$R_{13}$ is hydrogen, $C_1$-$C_4$alkyl, benzyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, or an alkali metal, alkaline earth metal, manganene, copper, zinc, cobalt, silver, nickel, ammonium or organic ammonium cation;

$R_1$ and $R_2$ are each independently hydrogen, methyl, ethyl, or $R_1$ may be taken together with R and the atoms to which they are attached to form a five membered saturated ring substituted with one to three $C_1$-$C_4$alkyl groups, and when taken together, $R_1$ and $R_2$ may form a ring in which $R_1R_2$ is represented by —$(CH_2)_t$— where t is an integer of 2, 3, 4, 5 or 6 with the proviso that when $R_1$ is methyl or ethyl then $R_2$ is hydrogen;

$R_3$ is hydrogen, $C_1$-$C_4$alkyl or hydroxy with the proviso that $R_3$ is hydroxy, $X_2$ is other than $C_1$-$C_4$alkyl, and further with the proviso that when $R_3$ is $C_1$-$C_4$alkyl, $X_1$ is other than hydrogen or methyl; and $R_4$ is $C_1$-$C_6$alkyl, $C_3$-$C_6$cycloalkyl, $C_1$-$C_6$haloalkyl, $C_2$-$C_6$alkenyl, $C_2$-$C_6$alkynyl, benzyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, or phenyl optionally substituted with one halogen, nitro, cyano, $C_1$-$C_4$alkyl, $C_1$-$C_4$haloalkyl, $C_1$-$C_4$alkoxy or $C_1$-$C_4$haloalkoxy group;

and the optical isomers and diastereomers thereof; and mixtures thereof.

This invention also relates to a method for the selective control of undesirable plant species in the presence of cereal crops using those compounds.

This invention also relates to herbicidal compositions comprising those compounds and an agronomically acceptable carrier.

DETAILED DESCRIPTION OF THE INVENTION

The present invention provides a method for controlling undesirable plant species which comprises applying to the foliage of said plants or to the soil, water, or other medium containing seeds or other propagating organs thereof, a herbicidally effective amount of a formula I or II benzodiazepine compound.

The present invention also provides methods and compositions for the selective control of undesirable plant species in the presence of cereal crops which comprises applying to the foliage and stems of the crops and undesirable plant species growing in the presence thereof or to the soil, water, or other medium containing seeds or other propagating organs of the undesirable plant species in which the crops are growing, an amount of a formula I or II benzodiazepine compound effective for the selective control of the undesirable plant species growing in the presence of the crops.

The benzodiazepine compounds useful in the methods and compositions of the present invention have the structural formula

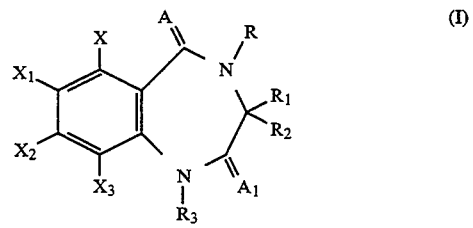

(I)

or

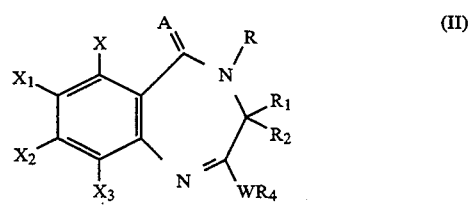

(II)

wherein X, $X_1$, $X_2$, $X_3$, A, $A_1$, W, R, $R_1$, $R_2$, $R_3$ and $R_4$ are as described hereinabove.

Preferred benzodiazepine herbicidal agents of the present invention are those wherein X and $X_2$ are hydrogen;

$X_1$ is hydrogen, halogen, methyl, $C_1$-$C_4$alkoxy or $C_2$-$C_3$alkynyl;

$X_3$ is hydrogen or methyl;

A is O;

$A_1$ and W are each independently O or S;

R is $C_3$-$C_6$cycloalkyl, $C_1$-$C_5$alkyl, phenyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups with the proviso that the para-position of the phenyl ring is not substituted, or R may be taken together with $R_1$ and the atoms to which they are attached to form a five membered saturated ring substituted with one to three $C_1$-$C_4$alkyl groups;

$R_1$ and $R_2$ are hydrogen or $R_1$ may be taken together with R and the atoms to which they are attached to form a five membered saturated ring substituted with one to three $C_1$-$C_4$alkyl groups;

$R_3$ is hydrogen or hydroxy; and $R_4$ is $C_1$-$C_6$alkyl, $C_3$-$C_6$cycloalkyl, $C_1$-$C_6$haloalkyl, $C_2$-$C_6$alkenyl, $C_2$-$C_6$alkynyl, benzyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, or phenyl optionally substituted with one halogen, nitro, cyano, $C_1$-$C_4$alkyl, $C_1$-$C_4$haloalkyl, $C_1$-$C_4$alkoxy or $C_1$-$C_4$haloalkoxy group.

More preferred herbicidal agents of the present invention are those wherein

X, $X_2$, $X_3$, $R_2$ and $R_3$ are hydrogen;

$X_1$ is hydrogen, halogen or methyl;

A, $A_1$ and W are O;

R is $C_3$-$C_6$cycloalkyl, $C_1$-$C_5$alkyl, or R may be taken together with $R_1$ and the atoms to which they are attached to form a five membered saturated ring substituted with one to three $C_1$-$C_4$alkyl groups;

$R_1$ is hydrogen or $R_1$ may be taken together with R and the atoms to which they are attached to form a five membered saturated ring substituted with one to three $C_1$-$C_4$alkyl groups; and $R_4$ is $C_1$-$C_6$alkyl.

Benzodiazepine compounds which are particularly effective herbicidal agents include 7-chloro-4-tert-butyl-3,4-dihydro-1H-1,4-benzodiazepine-2,5-dione;

7-chloro-1,2,3,11a-tetrahydro-3,3-dimethyl-5H-pyrrolo-[2,1-c][1,4]benzodiazepine-5,11(10H)-dione;

7-chloro-1,2,3,11a-tetrahydro-2,3,3-trimethyl-5H-pyrrolo[2,1-c][1,4]benzodiazepine-5,11(10H)-dione;

4-tert-butyl-3,4-dihydro-7-methyl-1H-1,4-benzodiazepine-2,5-dione;

7-chloro-3,4-dihydro-4-(2,2-dimethylpropyl)-1H-1,4-benzodiazepine-2,5-dione;

1,2,3,11a-tetrahydro-3,3,7-trimethyl-5H-pyrrolo-[2,1-c][1,4]benzodiazepine-5,11(10H)-dione;

7-bromo-4-tert-butyl-3,4-dihydro-1H-1,4-benzodiazepine-2,5-dione;

4-tert-butyl-3,4-dihydro-7,9-dimethyl-1H-1,4-benzodiazepine-2,5-dione;

4-tert-butyl-7-chloro-3,4-dihydro-2-thio-1H-1,4-benzodiazepine-2,5-dione;

4-tert-butyl-7-chloro-3,4-dihydro-9-methyl-1H-1,4-benzodiazepine-2,5-dione; and 4-tert-butyl-7-chloro-3,4-dihydro-2-methoxy-5H-1,4-benzodiazepin-5-one, among others.

Exemplary of halogen hereinabove are fluorine, chlorine, bromine and iodine. The term "$C_1$-$C_4$haloalkyl" is defined as a $C_1$-$C_4$alkyl group substituted with one or more halogen atoms. The term "$C_1$-$C_4$haloalkoxy" is defined as a $C_1$-$C_4$alkoxy group substituted with one or more halogen atoms. In formulas I and II above, alkali metals include: sodium, potassium and lithium. Alkaline earth metals of formulas I and II include magnesium and calcium. Further, the term "organic ammonium" contemplates agronomically acceptable substituents and may be defined as a group consisting of a positively charged nitrogen atom monovalently joined to from one to four aliphatic hydrocarbon groups, each containing from one to sixteen carbon atoms. Examples of other "medium" in which plants grow include hydroponics, synthetic polymer substrates, etc.

Certain benzodiazepine compounds of formula I may be prepared by reacting a 2-nitrobenzoyl chloride of formula III with an amino acid ester of formula IV wherein $R_{14}$ is $C_1$-$C_4$alkyl in the presence of a base to form a 2-nitrohippuric acid ester of formula V. Reduction of the nitro group of the formula V compound followed by in situ cyclization of the resultant 2-aminohippuric acid ester of formula Va affords the desired compound. The reaction scheme is shown in Flow Diagram I.

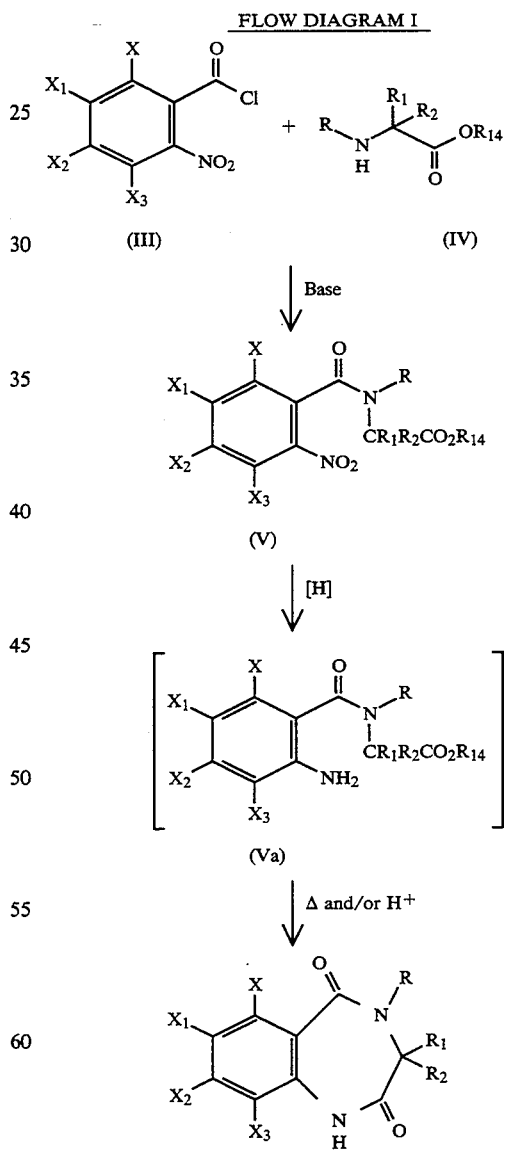

Advantageously, benzodiazepine compounds of formula II may be prepared from benzodiazepine compounds of formula I as shown in Flow Diagram II.

FLOW DIAGRAM II

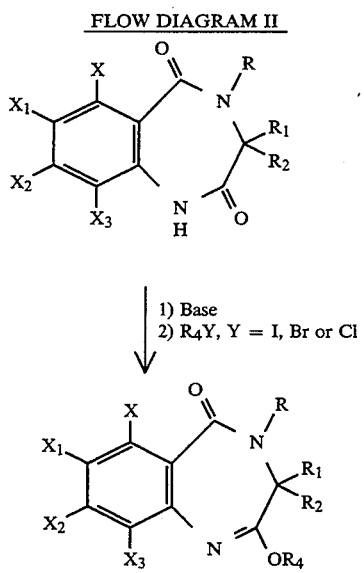

Alternatively, the benzodiazepine compounds of formulas I and II may be prepared according to conventional methods; see, for example, U.S. Pat. Nos. 3,681,341, 3,947,408, 3,985,732, 4,031,079, 4,185,016, 4,316,839, 4,352,815, 4,352,817 and 4,772,599; W. B. Wright, Jr., et al, Journal of Medicinal Chemistry, 21, pp. 1087–1089 (1978); P. J. McCloskey and A. G. Schultz, Journal of Organic Chemistry, 53, pp. 1380–1383 (1988); T. T. Tita and M. J. Kornet, Journal of Heterocyclic Chem-istry, 24, pp. 409–413 (1987); M. Mori, et al, Tetra-hedron, 42, pp. 3793–3806 (1986); T. Nagasaka, et al, Tetrahedron Letters, 30, pp. 1871–1872 (1989); A. G. Schultz, et al, Journal of the American Chemical Society, 109, pp. 6493–6502 (1987); E. Wolf and H. Kohl, Liebigs Ann. Chem., pp. 1245–1251 (1975); A. Kamal, Journal of Organic Chemistry, 56, pp. 2237–2240 (1991); R. Singh, et al, Indian Journal of Chemistry, 20B, pp. 129–131 (1981); and A. E. Azzouny, et al, Pharmazie, 32, pp. 318–323 (1977).

Unexpectedly, it has been found that the benzodiazepine compounds of formulas I and II are effective herbicidal agents useful for the control of a wide variety of undesirable plant species. Those compounds are effective for controlling weeds native to both dry land and wet land areas, especially when applied preemergence to the locus in which weed control is desired. The compounds are also useful as aquatic herbicides and are effective in controlling the above-said plants when applied to the foliage thereof or to the soil, water, or other medium containing seeds or other propagating organs thereof, such as stolons, tubers or rhizomes, at rates of from about 0.10 kg/ha to 10.0 kg/ha.

Advantageously, the benzodiazepine compounds of formulas I and II, especially 7-chloro-4-tert-butyl-3,4-dihydro-1H-1,4-benzodiazepine-2,5-dione and 7-chloro-1,2,3,11a-tetrahydro-3,3-dimethyl-5H-pyrrolo[2,1-c][1,4]-benzodiazepine-5,11(10H)-dione, are useful for the selective control of undesirable plant species in the presence of cereal crops such as corn, barley, wheat, oat, rye and rice. The compounds are particularly suitable for the selective control of undesirable plant species in the presence of corn. The compounds may be applied to the cereal crops and undesirable plant species or to the soil, water, or other medium containing seeds or other propagating organs of the undesirable plant species at rates of from about 0.10 kg/ha to 2.5 kg/ha.

While the herbicidal agents of this invention are effective for controlling undesirable plant species when employed alone, they may also be used in combination with other biological chemicals, including other herbicides.

The benzodiazepine compounds of formulas I and II may be applied in the form of a solid or liquid herbicidal composition, comprising a herbicidally effective amount of the formula I or formula II compound dispersed or dissolved in an agronomically acceptable solid or liquid carrier. The formulations may be applied as preemergence or postemergence treatments.

Advantageously, the herbicidal agents of the present invention may be formulated as emulsifiable concentrates, wettable powders, granular formulations, flowable concentrates and the like.

In order to facilitate a further understanding of the invention, the following examples are presented primarily for the purpose of illustrating more specific details thereof. The invention should not be deemed limited thereby except as defined in the claims.

EXAMPLE 1

Preemergence herbicidal evaluation of test compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.5 to 10.0 kg per hectare of test compound per cup. The treated cups are then placed on greenhouse benches, watered and cared for in accordance with standard greenhouse procedures. At four to five weeks after treatment, the tests are terminated and each cup is examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this preemergence herbicidal evaluation and in the postemergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
| --- | --- | --- |
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |

| Rating | Meaning | % Control Compared to Check |
|---|---|---|
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

PLANT SPECIES EMPLOYED IN HERBICIDAL EVALUATIONS

| Header Abb. | Common Name | Scientific Name |
|---|---|---|
| ABUTH | VELVETLEAF | ABUTILON THEOPHRASTI, MEDIC. |
| AMBEL | RAGWEED, COMMON | AMBROSIA ARTEMISII FOLIA, L. |
| IPOSS | MORNING-GLORY SPP. | IPOMOEA SPP. |
| SINAR | MUSTARD, WILD | BRASSICA KABER, (DC) L. C. WHEELR |
| SOLNI | NIGHTSHADE, BLACK | SOLANUM NIGRUM, L. |
| AVEFA | OAT, WILD | AVENA FATUA, L. |
| DIGSA | CRABGRASS, (HAIRY) L | DIGITARIA SANGUINALIS, (L) SCOP |
| SETVI | FOXTAIL, GREEN | SETARIA VIRIDIS, (L) BEAUV |
| GLXMAW | SOYBEAN, WILLIAMS | GLYCINE MAX(L)MERR. CV.WILLIAMS |
| GOSHI | COTTON | GOSSYPIUM HIRSUTUM, L. |
| ORYSAT | RICE, TEBONNET | ORYSA SATIVA, L. TEBONNET |
| TRZASK | WHEAT, SPRING, KATEP | TRICICUM AESTIVUM, KATEPWA |
| ZEAMX | CORN, FIELD | ZEA MAYS L. (SAMMEL-BEZEICHNUNG) |

COMPOUNDS EVALUATED AS HERBICIDAL AGENTS

| Compound Number | |
|---|---|
| 1 | 1,2,3,11a-Tetrahydro-3-methyl-5H-pyrrolo[2,1-c][1,4]benzodiazepine-5,11(10H)-dione |
| 2 | 7-Chloro-1,2,3,11a-tetrahydro-3,10-dimethyl-5H-pyrrolo[2,1-c][1,4]benzodiazepine-5,11(10H)-dione |
| 3 | cis-1,2,3,11a-Tetrahydro-3,10-dimethyl-5H-pyrrolo[2,1-c][1,4][benzodiazepine-5,11(10H)-dione |
| 4 | 1,2,3,11a-Tetrahydro-3,7-dimethyl-5H-pyrrolo-[2,1-c][1,4]benzodiazepine-5,11(10H)-dione |
| 5 | 7-Chloro-1,2,3,11a-tetrahydro-3-methyl-5H-pyrrolo[2,1-c][1,4]benzodiazepine-5,11(10H)-dione |
| 6 | 7-Chloro-1,2,3,11a-tetrahydro-2,10-dimethyl-5H-pyrrolo[2,1-c][1,4]benzodiazepine-5,11-(10H)-dione |
| 7 | 7-Chloro-1,2,3,11a-tetrahydro-3-methyl-11-thio-5H-pyrrolo[2,1-c][1,4]benzodiazepine-5,11(10H)-dione |
| 8 | 1,2,3,11a-Tetrahydro-3-methyl-11-thio-5H-pyrrolo[2,1-c][1,4]benzodiazepine-5,11(10H)-dione |
| 9 | 1,2,3,11a-Tetrahydro-7-methoxy-3-methyl-5H-pyrrolo[2,1-c][1,4]benzodiazepine-5,11(10H)-dione |
| 10 | cis-7-Chloro-1,2,3,11a-tetrahydro-3,9-dimethyl-5H-pyrrolo[2,1-c][1,4]benzodiazepine-5,11(10H)-dione |
| 11 | 1,2,3,11a-Tetrahydro-7-methoxy-3,10-dimethyl-5H-pyrrolo[2,1-c][1,4]benzodiazepine-5,11-(10H)-dione |
| 12 | trans-7-Chloro-1,2,3,11a-tetrahydro-3,10-dimethyl-5H-pyrrolo[2,1-c][1,4]benzodiazepine-5,11(10H)-dione |
| 13 | 1,2,3,11a-Tetrahydro-3,3-dimethyl-5H-pyrrolo-[2,1-c][1,4]benzodiazepine-5,11(10H)-dione |
| 14 | 7-Chloro-1,2,3,11a-tetrahydro-3,3-dimethyl-5H-pyrrolo[2,1-c][1,4]benzodiazepine-5,11(10H)-dione |
| 15 | 7-Chloro-3,4-dihydro-4-methyl-1H-1,4-benzodiazepine-2,5-dione |
| 16 | 7-Chloro-3,4-dihydro-4-isopropyl-3-methyl-1H-1,4-benzodiazepine-2,5-dione |
| 17 | 1,2,3,11aα-Tetrahydro-3β,9-dimethyl-5H-pyrrolo[2,1-c][1,4]benzodiazepine-5,11(10H)-dione |
| 18 | 7-Chloro-1,2,3,11a-tetrahydro-2,3,3-trimethyl-5H-pyrrolo[2,1-c][1,4]benzodiazepine-5,11(10H)-dione |
| 19 | 7-Chloro-1,2,3,11a-tetrahydro-10-hydroxy-2,3,3-trimethyl-5H-pyrrolo[2,1-c][1,4]-benzodiazepine-5,11(10H)-dione |
| 20 | 1,2,3,11a-Tetrahydro-2,3,3-trimethyl-5H-pyrrolo[2,1-c][1,4]benzodiazepine-5,11(10H)-dione |
| 21 | 7-Chloro-4-tert-butyl-3,4-dihydro-1H-1,4-benzodiazepine-2,5-dione |
| 22 | 4-Tert-butyl-3,4-dihydro-1H-1,4-benzodiazepine-2,5-dione |
| 23 | 7-Chloro-3,4-dihydro-4-isopropyl-1H-1,4-benzodiazepine-2,5-dione |
| 24 | 1,2,3,11a-Tetrahydro-3,3,9-trimethyl-5H-pyrrolo[2,1-c][1,4]benzodiazepine-5,11(10H)-dione |
| 25 | 7-Chloro-1,2,3,11a-tetrahydro-10-hydroxy-3,3-dimethyl-5H-pyrrolo[2,1-c][1,4]benzodiazepine-5,11(10H)-dione |
| 26 | 4-Tert-butyl-3,4-dihydro-9-methyl-1H-1,4-benzodiazepine-2,5-dione |
| 27 | 4-Tert-butyl-3,4-dihydro-7-methyl-1H-1,4-benzodiazepine-2,5-dione |
| 28 | 4-Tert-butyl-3,4-dihydro-7-methoxy-1H-1,4-benzodiazepine-2,5-dione |
| 29 | 7-Chloro-3,4-dihydro-4-(2,2-dimethylpropyl)-1H-1,4-benzodiazepine-2,5-dione |
| 30 | 7-Chloro-3,4-dihydro-4-isobutyl-1H-1,4-benzodiazepine-2,5-dione |
| 31 | 7-Chloro-4-cyclohexyl-3,4-dihydro-1H-1,4-benzodiazepine-2,5-dione |
| 32 | 4-Cyclopentyl-7-chloro-3,4-dihydro-1H-1,4-benzodiazepine-2,5-dione |
| 33 | 1,2,3,11a-Tetrahydro-7-methoxy-3,3-dimethyl-5H-pyrrolo[2,1-c][1,4]benzodiazepine-5,11(10H)-dione |
| 34 | 1,2,3,11a-Tetrahydro-3,3,7-trimethyl-5H-pyrrolo[2,1-c][1,4]benzodiazepine-5,11(10H)-dione |
| 35 | 7-Chloro-4-cyclobutyl-3,4-dihydro-1H-1,4-benzodiazepine-2,5-dione |
| 36 | 7-Chloro-3,4-dihydro-4-phenyl-1H-1,4-benzodiazepine-2,5-dione |
| 37 | 7-Chloro-3,4-dihydro-4-(1,1-dimethylpropyl)-1H-1,4-benzodiazepine-2,5-dione |
| 38 | 7-Bromo-4-tert-butyl-3,4-dihydro-1H-1,4-benzodiazepine-2,5-dione |
| 39 | 4-Tert-butyl-3,4-dihydro-7,9-dimethyl-1H-1,4-benzodiazepine-2,5-dione |
| 40 | 4-Tert-butyl-3,4-dihydro-7-iodo-1H-1,4-benzodiazepine-2,5-dione |
| 41 | 4-Tert-butyl-7-ethynyl-3,4-dihydro-1H-1,4-benzodiazepine-2,5-dione |
| 42 | 4-Tert-butyl-7-chloro-3,4-dihydro-2-thio-1H-1,4-benzodiazepine-2,5-dione |
| 43 | 4-Tert-butyl-7-chloro-3,4-dihydro-2-methoxy-5H-1,4-benzodiazepin-5-one |
| 44 | 4-Tert-butyl-7-chloro-3,4-dihydro-9-methyl-1H-1,4-benzodiazepine-2,5-dione |
| 45 | 7-Chloro-4-(o-chlorobenzyl)-3,4-dihydro-1H-1,4-benzodiazepine-2,5-dione |

TABLE I

Preemergence Herbicidal Evaluations of Test Compounds

| Compound Number | Rate (kg/ha) | ABUTH | AMBEL | IPOSS | SINAR | SOLNI | AVEFA | DIGSA | SETVI | GLXMAW | GOSHI | ORYSAT | TRZASK | ZEAMX |
|---|---|---|---|---|---|---|---|---|---|---|---|---|---|---|
| 1 | 4.0 | 9.0 | 7.0 | 9.0 | 9.0 | — | 8.0 | 6.0 | 7.0 | — | 8.0 | — | — | 2.0 |
|  | 1.0 | 5.0 | 4.5 | 8.0 | 6.5 | 4.0 | 3.0 | 0.0 | 2.5 | 4.0 | 3.5 | 2.0 | 0.0 | 1.0 |
| 2 | 10.0 | 5.0 | 9.0 | 9.0 | 9.0 | — | 1.0 | 2.0 | 2.0 | — | — | — | — | — |
|  | 4.0 | 1.0 | 9.0 | 7.0 | 8.0 | — | — | 3.0 | 0.0 | — | 0.0 | — | — | 0.0 |
| 3 | 10.0 | 3.0 | 6.0 | 3.0 | 6.0 | 7.0 | 1.0 | 0.0 | 1.0 | 8.0 | 2.0 | 2.0 | 6.0 | 2.0 |
| 4 | 1.0 | 9.0 | 6.0 | 9.0 | 8.5 | 7.0 | 6.5 | 8.0 | 8.5 | 4.0 | 6.3 | 3.0 | 0.0 | 0.0 |
|  | 0.5 | 6.0 | 2.5 | 5.0 | 7.0 | — | 3.0 | 5.0 | 3.5 | 9.0 | 2.0 | 3.0 | 7.0 | 2.3 |
| 5 | 1.0 | 9.0 | 9.0 | 9.0 | 9.0 | 9.0 | 9.0 | 8.0 | 6.7 | 2.0 | — | 2.0 | 4.0 | 0.7 |
|  | 0.5 | 8.3 | 5.7 | 9.0 | 8.7 | — | 4.5 | 6.0 | 4.7 | — | 0.0 | — | — | — |
| 6 | 5.0 | 5.0 | 3.0 | 6.0 | 7.0 | 9.0 | 3.0 | 6.0 | 1.0 | — | 0.0 | — | — | 2.0 |
| 7 | 1.0 | 9.0 | 9.0 | 9.0 | 9.0 | — | 0.0 | 8.0 | 6.0 | — | 7.0 | — | — | 0.0 |
| 8 | 0.5 | 3.0 | 9.0 | 8.0 | 5.0 | — | 8.0 | 5.0 | 1.0 | — | 0.0 | — | — | 5.0 |
|  | 4.0 | 9.0 | 0.0 | 6.0 | 9.0 | — | 1.0 | 0.0 | 6.0 | — | 0.0 | — | — | 0.0 |
| 9 | 1.0 | 5.0 | 8.0 | 8.0 | 8.0 | — | 2.0 | 7.0 | 0.0 | — | 3.0 | — | — | 0.0 |
|  | 4.0 | 9.0 | 3.0 | 9.0 | 9.0 | 9.0 | 0.0 | 3.0 | 0.0 | 6.0 | 0.0 | — | — | 6.0 |
| 10 | 1.0 | 8.0 | 8.0 | 9.0 | 8.0 | 9.0 | 8.5 | 9.0 | 2.0 | 6.0 | 2.5 | 5.0 | 8.0 | 3.5 |
|  | 0.5 | 7.5 | 5.5 | 7.5 | 8.5 | 7.0 | 3.0 | 8.0 | 7.0 | 5.0 | 1.0 | 3.0 | 3.0 | 1.0 |
| 11 | 10.0 | 6.0 | 6.0 | 8.0 | 9.0 | — | 1.0 | 2.0 | 3.5 | — | — | — | — | — |
| 12 | 10.0 | 3.0 | 6.0 | 6.0 | 7.0 | 9.0 | 1.0 | 0.0 | 0.0 | — | 0.0 | — | — | 3.0 |
| 14 | 1.0 | 8.5 | 8.7 | 8.8 | 9.0 | 9.0 | 7.9 | — | 8.7 | 8.3 | 7.1 | 3.3 | 7.9 | 3.0 |
|  | 0.5 | 7.6 | 8.2 | 8.8 | 9.0 | 8.7 | 6.6 | — | 7.1 | 6.7 | 4.4 | 2.8 | 5.9 | 1.8 |
| 15 | 10.0 | 8.0 | 0.0 | 6.0 | 7.0 | — | 0.0 | 0.0 | 0.0 | — | 0.0 | — | — | — |
| 16 | 4.0 | 9.0 | 8.0 | 9.0 | 9.0 | — | 8.0 | 8.0 | 8.0 | — | 6.0 | — | — | 6.0 |
|  | 1.0 | 4.7 | 2.7 | 6.0 | 6.3 | 3.0 | 1.3 | 1.0 | 1.3 | 4.5 | 1.7 | 0.5 | 1.0 | 0.0 |
| 17 | 1.0 | 2.0 | 2.0 | 6.0 | 9.0 | 4.0 | 0.0 | — | 4.0 | 1.0 | 2.0 | 0.0 | 0.0 | 0.0 |
| 18 | 1.0 | 4.0 | 5.0 | 8.0 | 9.0 | 8.0 | 2.0 | — | 2.0 | 2.0 | 1.0 | 0.0 | 1.0 | 0.0 |
|  | 0.5 | 2.0 | 2.0 | 1.0 | 9.0 | 9.0 | 1.0 | — | 1.0 | 3.0 | 1.0 | 0.0 | 1.0 | 0.0 |
| 19 | 1.0 | 9.0 | 2.0 | 9.0 | 9.0 | 7.0 | 0.0 | — | 2.0 | 5.0 | — | 2.0 | 0.0 | 0.0 |
| 20 | 0.5 | 9.0 | 4.0 | 9.0 | 9.0 | 9.0 | 0.0 | — | 4.0 | 8.3 | 2.0 | 4.9 | 0.0 | 4.5 |
| 21 | 1.0 | 9.0 | 8.8 | 8.9 | 9.0 | 8.9 | 7.8 | — | 8.8 | 7.9 | 9.0 | 3.9 | 7.4 | 3.0 |
|  | 0.5 | 9.0 | 8.7 | 9.0 | 9.0 | 9.0 | 7.2 | — | 8.4 | 7.0 | 8.7 | 3.0 | 7.0 | 2.0 |
| 22 | 1.0 | 8.0 | 9.0 | 9.0 | 7.0 | 3.0 | 8.0 | — | 7.0 | 6.0 | 9.0 | 2.0 | 3.0 | 0.0 |
|  | 0.5 | 6.0 | 9.0 | 9.0 | 9.0 | 6.0 | 4.0 | — | 1.0 | 7.0 | 5.0 | 2.0 | 1.0 | 0.0 |
| 23 | 1.0 | 9.0 | 9.0 | 9.0 | 9.0 | 9.0 | 3.0 | 0.0 | 0.0 | 6.0 | 9.0 | 2.0 | 2.0 | 0.0 |
| 24 | 1.0 | 7.0 | 8.0 | 9.0 | 9.0 | 8.0 | 4.0 | 8.0 | 1.0 | 8.0 | 2.0 | 2.0 | 0.0 | 0.0 |
| 25 | 1.0 | 2.0 | 7.0 | 6.0 | 8.0 | 8.5 | 2.0 | 5.0 | 0.0 | 2.0 | 1.0 | 2.0 | 2.0 | 0.0 |
| 26 | 1.0 | 9.0 | 8.0 | 8.0 | 8.0 | 8.0 | 8.0 | 1.0 | 6.0 | 9.0 | 9.0 | 4.0 | 8.0 | 4.0 |
|  | 0.5 | 9.0 | 6.0 | 9.0 | 9.0 | 8.5 | 7.0 | — | 9.0 | 7.0 | 7.0 | 3.0 | 7.0 | 1.0 |
| 27 | 1.0 | 8.5 | 8.0 | 8.0 | 9.0 | 8.5 | 8.0 | — | 9.0 | 7.5 | 9.0 | 4.5 | 5.0 | 3.5 |
|  | 0.5 | 8.5 | 6.0 | 4.0 | 9.0 | 7.0 | 1.0 | — | 0.0 | 7.5 | 8.5 | 3.0 | 5.0 | 2.0 |
| 28 | 1.0 | 8.0 | 8.0 | 9.0 | 0.0 | 9.0 | 6.0 | — | 3.5 | 2.0 | 7.0 | 0.0 | 0.0 | 0.0 |
| 29 | 1.0 | 9.0 | 6.0 | 0.0 | 8.5 | 7.0 | 1.0 | — | 1.0 | 6.0 | 9.0 | 6.0 | 6.0 | 4.5 |
|  | 0.5 | 5.0 | 8.5 | 9.0 | 0.0 | 9.0 | 6.0 | 9.0 | 0.0 | 4.5 | 9.0 | 3.5 | 2.0 | 3.0 |
| 30 | 1.0 | 1.0 | 5.5 | 0.0 | 0.0 | 0.0 | 4.0 | 9.0 | 1.0 | 3.0 | 9.0 | 0.0 | 0.0 | 0.0 |
| 31 | 1.0 | 6.0 | 0.0 | 4.0 | 9.0 | 7.0 | 0.0 | 0.0 | 0.0 | 6.0 | 6.0 | 6.0 | 2.0 | 4.0 |
| 32 | 4.0 | 9.0 | 7.0 | 0.0 | 9.0 | — | 3.0 | — | 6.0 | 3.0 | 3.0 | — | — | 1.0 |
|  | 1.0 | 9.0 | 8.0 | 6.0 | 9.0 | 9.0 | 8.0 | — | 8.0 | 6.0 | 2.0 | 4.0 | 0.0 | 6.0 |
| 33 | 0.75 | 9.0 | 2.0 | 4.0 | 8.0 | 8.0 | 2.0 | — | 4.0 | 0.0 | 4.0 | 2.0 | 0.0 | 0.0 |
| 34 | 1.0 | 9.0 | 9.0 | 9.0 | 9.0 | 9.0 | 7.0 | — | 9.0 | 7.0 | 6.0 | 4.0 | 4.0 | 3.0 |

TABLE I-continued

Preemergence Herbicidal Evaluations of Test Compounds

| Compound Number | Rate (kg/ha) | ABUTH | AMBEL | IPOSS | SINAR | SOLNI | AVEFA | DIGSA | SETVI | GLXMAW | GOSHI | ORYSAT | TRZASK | ZEAMX |
|---|---|---|---|---|---|---|---|---|---|---|---|---|---|---|
| 35 | 0.5 | 9.0 | 6.0 | 9.0 | 9.0 | 9.0 | 3.0 | — | 4.0 | 7.0 | 4.0 | 3.0 | 1.0 | 1.0 |
|  | 1.0 | 9.0 | 8.0 | 2.0 | 9.0 | 8.0 | 4.0 | — | 7.0 | 3.0 | 8.0 | 3.0 | 4.0 | 0.0 |
| 36 | 0.5 | 8.0 | 8.0 | 1.0 | 9.0 | 8.0 | 2.0 | — | 2.0 | 1.0 | 4.0 | 2.0 | 2.0 | 0.0 |
|  | 1.0 | 6.0 | 6.0 | 8.0 | 9.0 | 8.0 | 4.0 | — | 6.0 | 6.0 | 7.0 | 4.0 | 0.0 | 0.0 |
| 37 | 0.5 | 2.0 | 4.0 | 7.0 | 9.0 | 8.0 | 2.0 | — | 4.0 | 3.0 | 4.0 | 1.0 | 0.0 | 0.0 |
|  | 1.0 | 9.0 | 8.0 | 4.0 | 9.0 | 8.0 | 4.0 | — | 6.0 | 6.0 | 7.0 | 3.0 | 6.0 | 2.0 |
| 38 | 0.5 | 7.0 | 6.0 | 4.0 | 9.0 | 7.0 | 2.0 | — | 3.0 | 6.0 | 4.0 | 2.0 | 4.0 | 1.0 |
|  | 1.0 | 9.0 | 9.0 | 9.0 | 9.0 | 9.0 | 9.0 | — | 9.0 | 9.0 | 9.0 | 7.0 | 9.0 | 6.0 |
| 39 | 0.5 | 8.0 | 8.0 | 9.0 | 9.0 | 9.0 | 7.0 | — | 7.0 | 9.0 | 9.0 | 4.0 | 7.0 | 4.0 |
|  | 1.0 | 9.0 | 7.0 | 9.0 | 9.0 | 9.0 | 9.0 | — | 9.0 | 9.0 | 9.0 | 7.0 | 9.0 | 7.0 |
| 40 | 0.5 | 7.0 | 0.0 | 0.0 | — | 4.0 | 9.0 | — | 9.0 | 0.0 | 0.0 | 7.0 | 0.0 | 3.0 |
| 41 | 1.0 | 0.0 | 6.0 | 8.0 | 9.0 | 8.0 | 0.0 | — | 0.0 | 7.0 | 9.0 | 3.0 | 2.0 | 0.0 |
|  | 1.0 | 8.0 | 4.0 | 8.0 | 9.0 | 6.0 | 4.0 | — | 9.0 | 6.0 | 2.0 | 2.0 | 0.0 | 0.0 |
| 42 | 0.5 | 4.0 | 6.0 | 8.0 | 9.0 | 9.0 | 2.0 | — | 2.0 | 7.0 | 9.0 | 6.0 | 7.0 | 5.0 |
|  | 1.0 | 9.0 | 8.0 | 8.0 | 9.0 | 9.0 | 7.0 | — | 9.0 | 6.0 | 9.0 | 6.0 | 7.0 | 4.0 |
| 43 | 0.5 | 2.0 | 7.0 | 9.0 | 9.0 | 7.0 | 6.0 | — | 9.0 | 3.0 | 2.0 | 3.0 | 3.0 | 2.0 |
| 44 | 1.0 | 4.0 | 7.0 | 6.0 | 9.0 | 7.0 | 5.0 | — | 6.0 | 3.0 | 5.0 | 2.0 | 2.0 | 1.0 |
| 45 | 1.0 | 0.0 | 0.0 | 0.0 | 9.0 | 9.0 | 0.0 | — | 0.0 | 0.0 | 0.0 | 0.0 | 0.0 | 0.0 |

EXAMPLE 2

Postemergence herbicidal evaluation of test compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 0.5 kg to 10.0 kg per hectare of test compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 1.

The data obtained are reported in Table II below. The compounds evaluated are reported by compound number given in Example 1.

TABLE II

Postemergence Herbicidal Evaluations of Test Compounds

| Compound Number | Rate (kg/ha) | ABUTH | AMBEL | IPOSS | SINAR | SOLNI | AVEFA | DIGSA | SETVI | GLXMAW | GOSHI | ORYSAT | TRZASK | ZEAMX |
|---|---|---|---|---|---|---|---|---|---|---|---|---|---|---|
| 1 | 10.0 | 3.0 | 0.0 | 3.0 | 5.0 | — | 0.0 | 0.0 | 0.0 | 4.0 | 4.0 | 0.0 | 0.0 | 0.0 |
|   | 1.0 | 0.0 | 0.0 | 0.0 | 2.0 | 4.0 | 0.0 | — | 0.0 | — | — | — | — | — |
| 2 | 10.0 | 1.0 | 0.0 | 2.0 | 2.0 | — | 0.0 | 0.0 | 0.0 | — | — | — | — | — |
| 3 | 10.0 | 1.0 | 4.0 | 0.0 | 1.0 | — | 0.0 | 0.0 | 0.0 | — | — | — | — | 3.0 |
| 4 | 4.0 | 9.0 | 9.0 | 9.0 | 9.0 | 2.0 | 0.0 | 0.0 | 2.0 | 3.0 | 5.0 | 0.0 | 0.0 | 0.5 |
|   | 1.0 | 6.5 | 4.5 | 4.5 | 7.5 | 8.0 | 2.5 | 0.0 | 0.0 | 7.0 | 4.0 | 2.0 | 1.0 | 0.8 |
| 5 | 1.0 | 4.5 | 4.5 | 6.8 | 6.5 | 7.0 | 1.0 | 1.0 | 3.0 | 6.0 | 8.5 | 0.0 | 1.0 | 0.5 |
|   | 0.5 | 4.5 | 1.3 | 4.8 | 6.0 | — | 0.0 | 0.7 | 2.3 | — | 6.8 | — | — | — |
| 6 | 5.0 | 0.0 | 0.0 | 2.0 | 2.0 | — | 0.0 | 0.0 | 0.0 | — | — | — | — | — |
| 7 | 10.0 | 1.0 | 3.0 | 5.0 | 2.0 | — | 0.0 | 1.0 | 0.0 | — | — | — | — | 1.0 |
| 8 | 10.0 | 3.0 | 7.0 | 3.0 | 2.0 | — | 0.0 | 0.0 | 6.0 | — | 6.0 | 1.0 | 1.0 | 0.0 |
| 9 | 10.0 | 9.0 | 9.0 | 8.0 | 9.0 | — | 5.0 | 3.0 | 1.0 | — | 9.0 | — | — | 0.0 |
|   | 4.0 | 7.0 | 6.0 | 9.0 | 9.0 | — | 1.0 | 0.0 | 3.0 | 4.0 | 6.5 | 1.0 | 1.0 | — |
| 10 | 4.0 | 7.0 | 5.0 | 9.0 | 3.5 | 4.0 | 1.0 | 2.0 | 1.0 | — | — | — | — | — |
|    | 1.0 | 5.0 | 1.0 | 5.0 | 2.0 | — | 0.0 | 0.0 | 3.0 | — | — | — | — | — |
| 11 | 10.0 | 1.0 | 0.0 | 2.0 | 2.0 | — | 0.0 | 0.0 | 0.0 | — | — | — | — | — |
| 12 | 10.0 | 2.0 | 0.0 | 1.0 | 2.0 | 4.0 | 0.0 | 0.0 | 0.0 | 4.0 | 5.0 | 2.0 | 2.9 | 3.0 |
| 13 | 4.0 | 4.0 | 2.0 | 7.0 | 2.0 | 9.0 | 2.0 | 5.3 | 6.0 | 6.0 | 8.1 | 2.1 | 1.7 | 1.6 |
| 14 | 1.0 | 7.7 | 7.8 | 8.4 | 9.0 | 8.8 | 4.3 | 2.3 | 5.6 | 7.9 | 8.3 | 1.0 | — | 1.0 |
|    | 0.5 | 6.4 | 7.0 | 7.0 | 8.8 | — | 2.9 | 3.0 | 3.0 | 6.9 | — | — | — | — |
| 15 | 10.0 | 1.0 | 0.0 | 2.0 | 3.0 | — | 0.0 | — | 0.0 | — | 7.0 | 0.0 | 0.0 | 0.0 |
| 16 | 10.0 | 3.0 | 7.0 | — | 9.0 | 4.0 | 7.0 | — | 3.0 | 7.0 | 7.0 | 0.0 | 2.0 | 0.0 |
| 17 | 1.0 | 7.0 | 2.0 | 4.0 | 4.0 | 9.0 | 0.0 | — | 8.0 | 7.0 | 4.0 | 0.0 | 1.0 | 0.0 |
| 18 | 1.0 | 9.0 | 6.0 | 8.0 | 9.0 | 9.0 | 1.0 | — | 5.0 | 1.0 | 7.0 | 1.0 | 0.0 | 0.0 |
| 19 | 1.0 | 4.0 | 4.0 | 8.0 | 8.0 | 9.0 | 2.0 | — | 2.0 | 7.0 | 7.0 | 0.0 | 0.0 | 2.0 |
| 20 | 1.0 | 4.0 | 2.0 | 9.0 | 8.0 | 9.0 | 5.5 | — | 9.0 | 8.4 | 9.0 | 2.4 | 2.0 | 3.9 |
| 21 | 0.5 | 9.0 | 8.3 | 8.5 | 9.0 | 9.0 | 4.0 | — | 7.8 | 8.0 | 8.8 | 2.2 | 5.0 | 3.0 |
|    | 0.5 | 9.0 | 7.4 | 7.9 | 9.0 | 9.0 | 0.0 | — | 6.0 | 7.0 | 9.0 | 3.0 | 3.2 | 1.0 |
| 22 | 0.5 | 8.0 | 4.0 | 7.0 | 9.0 | 9.0 | 0.0 | — | 0.0 | 5.0 | 7.0 | 1.0 | 3.0 | 0.0 |
|    | 1.0 | 6.0 | 2.0 | 4.0 | 4.0 | 4.0 | 0.0 | — | 0.0 | 3.0 | 2.0 | 0.0 | 1.0 | 0.0 |
| 23 | 1.0 | 4.0 | 0.0 | 6.0 | 9.0 | 9.0 | 0.0 | 2.0 | 0.0 | 2.0 | 2.0 | 0.0 | 0.0 | 0.0 |
| 24 | 1.0 | 0.0 | 0.0 | 2.0 | 4.0 | 9.0 | 7.0 | — | 4.0 | 3.0 | 3.0 | 0.0 | 0.0 | 1.0 |
| 25 | 1.0 | 9.0 | 0.0 | 0.0 | 6.0 | 0.0 | 2.0 | — | 1.0 | 2.0 | 6.0 | 0.0 | 4.0 | 0.0 |
| 26 | 0.5 | 9.0 | 6.0 | 8.0 | 9.0 | 9.0 | 2.0 | — | 0.0 | 6.0 | 6.0 | 4.0 | 3.0 | 0.0 |
| 27 | 1.0 | 9.0 | 1.0 | 4.0 | 8.0 | 9.0 | 6.5 | — | 1.0 | 3.0 | 8.5 | 2.0 | 4.0 | 1.0 |
|    | 0.5 | 8.0 | 8.5 | 8.5 | 9.0 | 9.0 | 3.5 | — | 7.5 | 8.0 | 2.5 | 5.0 | 3.0 | 1.5 |
| 28 | 1.0 | 8.0 | 7.0 | 8.0 | 9.0 | 8.0 | 1.0 | — | 6.0 | 2.0 | 7.0 | 3.0 | 4.0 | 0.0 |
| 29 | 1.0 | 8.0 | 6.0 | 4.0 | 8.0 | 9.0 | 2.0 | — | 0.0 | 3.0 | — | 0.0 | 1.0 | 2.0 |
| 30 | 1.0 | 8.0 | 8.0 | 9.0 | 7.0 | — | 2.0 | — | 0.0 | 1.0 | 6.0 | 4.0 | 0.0 | 1.0 |
|    | 0.5 | 4.0 | 2.0 | 8.0 | 9.0 | 6.0 | 2.0 | — | 0.0 | 3.0 | 9.0 | 1.0 | 6.0 | 0.0 |
| 31 | 1.0 | 9.0 | 4.0 | 7.0 | 9.0 | 8.0 | 2.0 | — | 4.0 | 1.0 | 9.0 | 0.0 | 2.0 | 0.0 |
| 32 | 4.0 | 9.0 | 2.0 | 6.0 | 9.0 | 9.0 | 0.0 | — | 0.0 | 4.0 | 8.0 | 0.0 | 0.0 | 0.0 |
|    | 1.0 | 4.0 | 2.0 | 9.0 | 9.0 | — | 0.0 | — | 0.0 | 2.0 | 6.0 | — | — | 2.0 |
| 33 | 0.75 | 9.0 | 8.0 | 9.0 | 9.0 | 7.0 | 0.0 | — | 9.0 | 4.0 | 6.0 | 0.0 | 0.0 | 0.0 |
| 34 | 1.0 | 4.0 | 7.0 | 9.0 | 9.0 | 6.0 | 0.0 | — | 0.0 | 8.0 | 9.0 | 2.0 | 2.0 | 2.0 |
|    | 0.5 | 8.0 | 7.0 | 9.0 | 9.0 | 8.0 | 0.0 | — | 6.0 | 6.0 | 6.0 | 1.0 | 2.0 | 1.0 |
| 35 | 1.0 | 9.0 | 6.0 | 4.0 | 9.0 | 9.0 | 0.0 | — | 0.0 | 4.0 | 6.0 | 1.0 | 2.0 | 0.0 |

TABLE II-continued

Postemergence Herbicidal Evaluations of Test Compounds

| Compound Number | Rate (kg/ha) | ABUTH | AMBEL | IPOSS | SINAR | SOLNI | AVEFA | DIGSA | SETVI | GLXMAW | GOSHI | ORYSAT | TRZASK | ZEAMX |
|---|---|---|---|---|---|---|---|---|---|---|---|---|---|---|
| 36 | 0.5 | 9.0 | 4.0 | 4.0 | 9.0 | 9.0 | 0.0 | — | 0.0 | 4.0 | 5.0 | 0.0 | 2.0 | 0.0 |
|    | 1.0 | 9.0 | 4.0 | 9.0 | 9.0 | 8.0 | 4.0 | — | 2.0 | 4.0 | 9.0 | 2.0 | 2.0 | 2.0 |
| 37 | 0.5 | 7.0 | 3.0 | 7.0 | 9.0 | 6.0 | 2.0 | — | 1.0 | 3.0 | 9.0 | 0.0 | 2.0 | 1.0 |
|    | 1.0 | 9.0 | 6.0 | 6.0 | 9.0 | 6.0 | 0.0 | — | 2.0 | 6.0 | 8.0 | 0.0 | 0.0 | 0.0 |
| 38 | 0.5 | 6.0 | 2.0 | 2.0 | 6.0 | 4.0 | 0.0 | — | 1.0 | 4.0 | 8.0 | 2.0 | 2.0 | 0.0 |
|    | 1.0 | 9.0 | 9.0 | 8.0 | 9.0 | 9.0 | 3.0 | — | 9.0 | 9.0 | 9.0 | 0.0 | 2.0 | 2.0 |
| 39 | 0.5 | 8.0 | 4.0 | 7.0 | 9.0 | 9.0 | 2.0 | — | 4.0 | 6.0 | 8.0 | 3.0 | 2.0 | 2.0 |
|    | 1.0 | 9.0 | 7.0 | 9.0 | 9.0 | 9.0 | 4.0 | — | 9.0 | 8.0 | 9.0 | 2.0 | 2.0 | 2.0 |
| 40 | 0.5 | 6.0 | 6.0 | 9.0 | 9.0 | 9.0 | 3.0 | — | 4.0 | 7.0 | 9.0 | 3.0 | 2.0 | 2.0 |
| 41 | 1.0 | 7.0 | 4.0 | 0.0 | 6.0 | 9.0 | 0.0 | — | 4.0 | 5.0 | 7.0 | 2.0 | 0.0 | 0.0 |
| 42 | 1.0 | 0.0 | 2.0 | 8.0 | 9.0 | — | 0.0 | 6.0 | 0.0 | 6.0 | 3.0 | 0.0 | 2.0 | 0.0 |
|    | 1.0 | 5.0 | 9.0 | 6.0 | 6.0 | 2.0 | 4.0 | — | 9.0 | 6.0 | 9.0 | 4.0 | 4.0 | 2.0 |
| 43 | 0.5 | 3.0 | 7.0 | 8.0 | 8.0 | — | 5.0 | — | 6.0 | 0.0 | 2.0 | 0.0 | 0.0 | 0.0 |
|    | 1.0 | 5.0 | 7.0 | 5.0 | 7.0 | 7.0 | 2.0 | — | 9.0 | 9.0 | 5.0 | 2.0 | 3.0 | 1.0 |
| 44 | 1.0 | 2.0 | 3.0 | 4.0 | 6.0 | 9.0 | 0.0 | — | 2.0 | 2.0 | 2.0 | 0.0 | 0.0 | 0.0 |
| 45 | 1.0 | 7.0 | 9.0 | 3.0 | 9.0 | 9.0 | 0.0 | — | 0.0 | 3.0 | 6.0 | 0.0 | 2.0 | 2.0 |
|    | 0.5 | 2.0 | 8.0 | 2.0 | 9.0 | 8.0 | 0.0 | — | 0.0 | 3.0 | 6.0 | 0.0 | 2.0 | 2.0 |

EXAMPLE 3

Preparation of 5-Chloro-2-nitrobenzoyl chloride

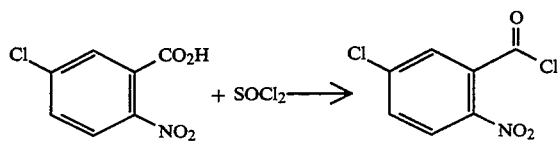

A mixture of thionyl chloride (7.25 mL, 99.5 mmol) and N,N-dimethylformamide is added to a mixture of 5-chloro-2-nitrobenzoic acid in toluene. The reaction mixture is heated to and held at 80° C. for 16 hours, cooled to room temperature, concentrated in vacuo, diluted with toluene, concentrated in vacuo and diluted with toluene to obtain the title product as a 1 molar solution in toluene.

Using essentially the same procedure, but using the appropriately substituted 2-nitrobenzoic acid, the following compounds are obtained:

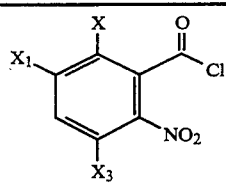

| X   | $X_1$ | $X_3$ |
|-----|-------|-------|
| H   | H     | H     |
| H   | H     | $CH_3$ |
| H   | $CH_3$ | H     |
| $CH_3$ | H | H     |
| H   | $OCH_3$ | H   |
| H   | $CH_3$ | $CH_3$ |

EXAMPLE 4

Preparation of Methyl N-tert-butylglycinate $(CH_3)_3CNH_2 + BrCH_2CO_2CH_3 \rightarrow (CH_3)_3CNHCH_2CO_2CH_3$ Methyl bromoacetate (7.1 mL, 75 mmol) is added dropwise to tert-butylamine (31.5 mL, 300 mmol) at 0° C. The reaction mixture is diluted with ether, warmed to room temperature and filtered. The filtrate is concentrated in vacuo to obtain the title product as a clear liquid (10.52 g) which is identified by $^1H$ and $^{13}CNMR$ spectral analyses.

Using essentially the same procedure, but using the appropriately substituted amine and methyl bromoacetate, the following compounds are obtained:

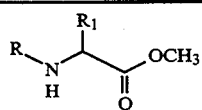

| R           | $R_1$ |
|-------------|-------|
| $CH(CH_3)_2$ | $CH_3$ |
| $CH_2C(CH_3)_3$ | H   |

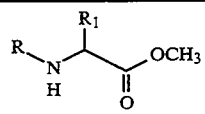

| R | $R_1$ |
|---|-------|
| 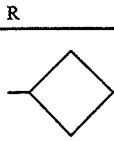 | H |
| 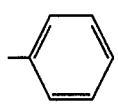 | H |
| $CH(CH_3)_2$ | H |
| $CH_2CH(CH_3)_2$ | H |
| 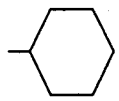 | H |
| 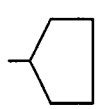 | H |
| $C(CH_3)_2CH_2CH_3$ | H |
| $CH_2C(CH_3)_3$ | $CH_3$ |

EXAMPLE 5

Preparation of Methyl β-tert-butyl-5-chloro-2-nitrohippurate

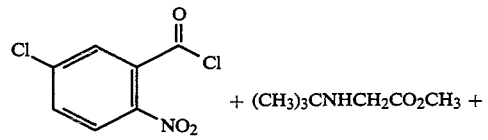 + $(CH_3)_3CNHCH_2CO_2CH_3$ +

$(C_2H_5)_3N \longrightarrow$ 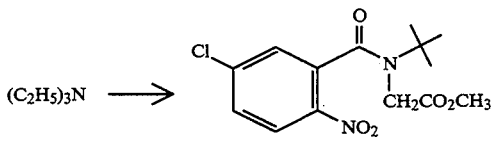

A 1 molar solution of 5-chloro-2-nitrobenzoyl chloride in toluene (20 mL, 20 mmol) is added to a mixture of methyl N-tert-butylglycinate (2.17 g, 15 mmol) and triethylamine (5.2 g, 37.5 mmol) in tetrahydrofuran at 0° C. The reaction mixture is stirred overnight at room temperature and poured into an ethyl acetate/water mixture. Tetrahydrofuran and methylene chloride are added to the mixture and the phases are separated. The organic phase is washed sequentially with 10% hydrochloric acid, saturated sodium hydrogen carbonate solution and brine, dried over anhydrous sodium sulfate and concentrated in vacuo to obtain an off-white solid. The solid is recrystallized from an ethanol/water mixture to give the title product as white needles (3.25 g, mp 155°–156° C.).

Using essentially the same procedure, but using the appropriately substituted 2-nitrobenzoyl chloride and methyl glycinate, the following compounds are obtained:

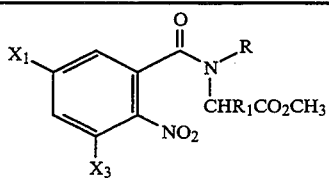

| X₁ | X₃ | R | R₁ |
|---|---|---|---|
| Cl | H | CH(CH₃)₂ | CH₃ |
| H | H | C(CH₃)₃ | H |
| H | CH₃ | C(CH₃)₃ | H |
| CH₃ | H | C(CH₃)₃ | H |
| Cl | H | CH₂C(CH₃)₃ | H |
| Cl | H | cyclobutyl | H |
| Cl | H | phenyl | H |
| Cl | H | CH(CH₃)₂ | H |
| OCH₃ | H | C(CH₃)₃ | H |
| Cl | H | CH₂CH(CH₃)₂ | H |
| Cl | H | cyclohexyl | H |
| Cl | H | cyclopentyl | H |
| Cl | H | C(CH₃)₂CH₂CH₃ | H |
| CH₃ | CH₃ | C(CH₃)₃ | H |
| Cl | H | CH₂C(CH₃)₃ | CH₃ |

EXAMPLE 6

Preparation of 7-Chloro-4-tert-butyl-3,4-dihydro-1H-1,4-benzodiazepine-2,5-dione

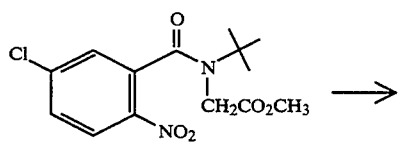

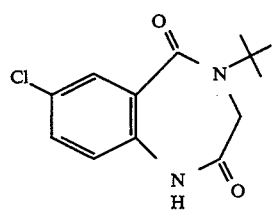

A mixture of methyl β-tert-butyl-5-chloro-2-nitrohippurate (2.45 g, 7.5 mmol) and 5% platinum on carbon (0.98 g, 40 wt % of 5% Pt/C) in a 1:1 tetrahydrofuran-/ethanol solution is shaken in a Parr Hydrogenator under a hydrogen pressure of 50 psi until 18.5 psi is taken up. The reaction mixture is filtered and the filtrate is concentrated in vacuo to give an oil. The oil is heated at reflux for 26 hours, cooled to room temperature and concentrated in vacuo to obtain an amber oil. The oil is dissolved in ethyl acetate and the resultant solution is concentrated in vacuo to form a solid. The solid is recrystallized from ethyl acetate/hexanes to give the title product as white needles (1.21 g, mp 177°–178° C.).

Using essentially the same procedure, but using the appropriately substituted methyl 2-nitrohippurate, the following compounds are obtained:

| X₁ | X₃ | R | R₁ | mp °C. |
|---|---|---|---|---|
| Cl | H | CH(CH₃)₂ | CH₃ | 228–230 |
| H | H | C(CH₃)₃ | H | 183–184 |
| H | CH₃ | C(CH₃)₃ | H | 169–171.5 |
| CH₃ | H | C(CH₃)₃ | H | 156–157 |
| Cl | H | CH₂C(CH₃)₃ | H | 195–196 |
| Cl | H | cyclobutyl | H | 205–206 |
| Cl | H | phenyl | H | 222–224 |
| Cl | H | CH(CH₃)₂ | H | 203–205 |
| OCH₃ | H | C(CH₃)₃ | H | 196–198 |
| Cl | H | CH₂CH(CH₃)₂ | H | 203.5–205.5 |
| Cl | H | cyclohexyl | H | 238–239 |
| Cl | H | cyclopentyl | H | 215.5–217 |
| Cl | H | C(CH₃)₂CH₂CH₃ | H | 149–151 |
| CH₃ | CH₃ | C(CH₃)₃ | H | 186–187 |
| Cl | H | CH₂C(CH₃)₃ | CH₃ | 153–154 |

EXAMPLE 7

Preparation of
7-Bromo-4-tert-butyl-3,4-dihydro-1H-1,4-benzodiazepine-2,5-dione

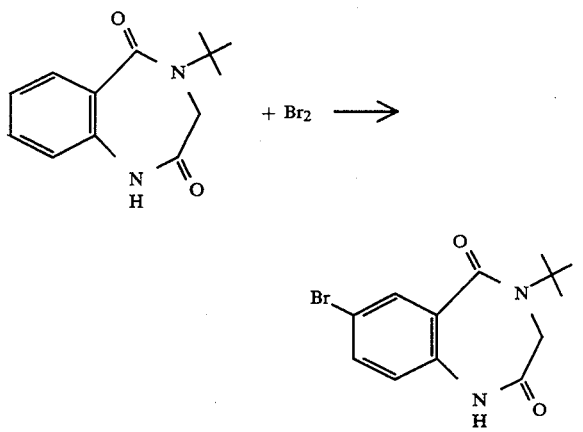

Bromine (1.72 g, 10.8 mmol) is added to a mixture of 4-tert-butyl-3,4-dihydro-1H-1,4-benzodiazepine-2,5-dione (1.0 g, 4.3 mmol) and sodium acetate (0.39 g, 4.8 mmol) in acetic acid. The reaction mixture is stirred at room temperature for 29 hours, concentrated in vacuo, diluted with ethyl acetate, washed sequentially with 0.1N sodium hydroxide solution and brine, dried over anhydrous sodium sulfate and concentrated in vacuo to give a residue. Chromatography of the residue using silica gel and 20% to 25% ethyl acetate in hexanes solutions gives the title product as a white solid (0.86 g, mp 205°–208° C.).

EXAMPLE 8

Preparation of
4-Tert-butyl-3,4-dihydro-7-iodo-1H-1,4-benzodiazepine-2,5-dione

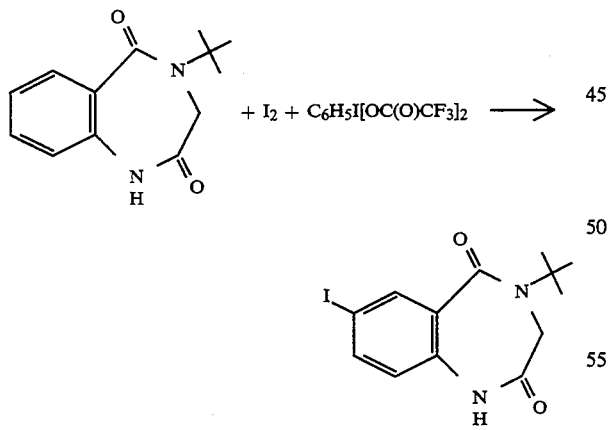

Bis(trifluoroacetoxy)phenyl iodine (2.05 g, 4.7 mmol) is added to a solution of 4-tert-butyl-3,4-dihydro-1H-1,4-benzodiazepine-2,5-dione (1.0 g, 4.3 mmol) and iodine (1.1 g, 4.3 mmol) in methylene chloride. The reaction mixture is stirred overnight at room temperature, diluted with ethyl acetate, washed sequentially with saturated sodium hydrogen carbonate solution, 1N sodium thiosulfate solution and brine, dried over anhydrous sodium sulfate and concentrated in vacuo to obtain a residue. Chromatography of the residue using silica gel and 20% to 25% ethyl acetate in hexanes solutions gives the title product as a beige solid (0.9 g, mp 230°–232° C.).

EXAMPLE 9

Preparation of
4-Tert-butyl-3,4-dihydro-7-[(trimethylsilyl)ethynyl]-1H-1,4-benzodiazepine-2,5-dione

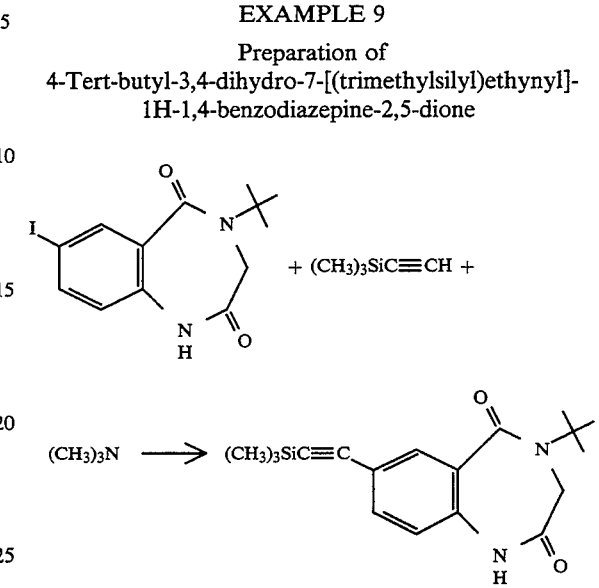

(Trimethylsilyl)acetylene (1.18 mL, 8.4 mmol), copper(I) iodide (0.05 g, 0.28 mmol) and bis(triphenylphosphine)palladium(II) chloride (0.1 g, 0.14 mmol) are added sequentially to a degassed suspension of 4-tert-butyl-3,4-dihydro-7-iodo-1H-1,4-benzodiazepine-2,5-dione (2.5 g, 7.0 mmol) in triethylamine. The reaction mixture is stirred at room temperature for 5 hours and filtered. The filtrate is diluted with ether and concentrated in vacuo to obtain a solid. Chromatography of the solid using silica gel and 15% to 20% ethyl acetate in hexanes solutions gives the title product as a light brown solid (1.33 g, mp 243°–244° C.).

EXAMPLE 10

Preparation of
4-Tert-butyl-7-ethynyl-3,4-dihydro-1H-1,4-benzodiazepine-2,5-dione

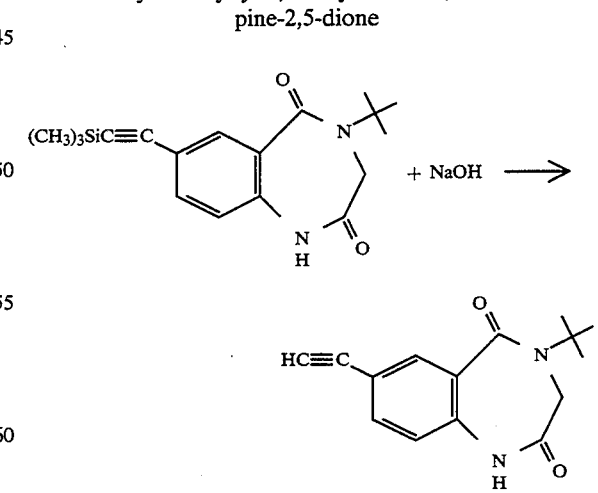

1N Sodium hydroxide solution (3.4 mL) is added to a suspension of 4-tert-butyl-3,4-dihydro-7-[(trimethylsilyl)ethynyl]-1H-1,4-benzodiazepine-2,5-dione (1.0 g, 3.0 mmol) in methanol. The reaction mixture is stirred at room temperature for 2 hours, concentrated in vacuo and extracted with ethyl acetate. The combined organic extracts are washed with brine, dried over anhydrous sodium sulfate and concentrated in vacuo to give the title product as a light brown solid (0.66 g, mp 216°–219° C.).

EXAMPLE 11

Preparation of 4-Tert-butyl-7-chloro-3,4-dihydro-2-thio-1H-1,4-benzodiazepine-2,5-dione

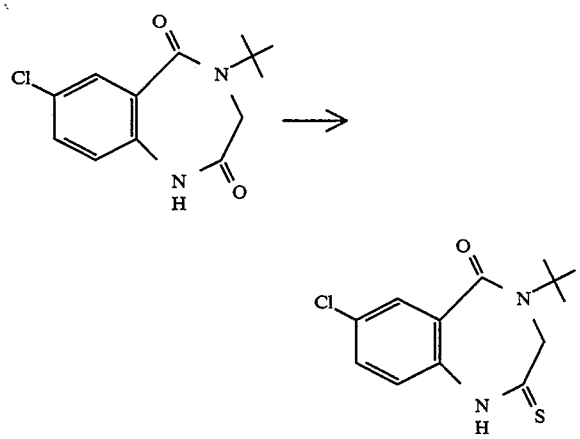

A mixture of 7-chloro-4-tert-butyl-3,4-dihydro-1H-1,4-benzodiazepine-2,5-dione (0.5 g, 1.9 mmol) and 2,4-bis(4-methoxyphenyl)-1,3-dithia-2,4-diphosphetane-2,4-disulfide (0.42 g, 1.0 mmol) in toluene is heated at reflux for 30 minutes, treated with additional 2,4-bis(4-methoxyphenyl)-1,3-dithia-2,4-diphosphetane-2,4-disulfide (0.42 g, 1.0 mmol), heated at reflux for 1 hour, cooled and concentrated in vacuo to obtain a residue. Flash column chromatography of the residue using silica gel and 20% to 40% ethyl acetate in hexanes solutions gives the title product as a yellow solid (0.34 g, mp 196°–197° C.).

EXAMPLE 12

Preparation of 4-Tert-butyl-7-chloro-3,4-dihydro-2-methoxy-5H-1,4-benzodiazepin-5-one

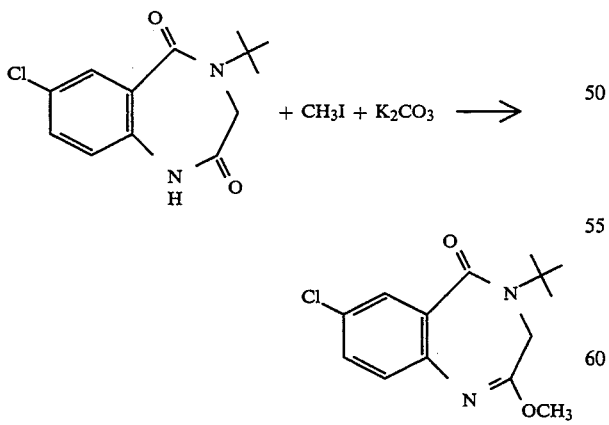

Methyl iodide (233 μL, 3.7 mmol) is added to a mixture of 7-chloro-4-tert-butyl-3,4-dihydro-1H-1,4-benzodiazepine-2,5-dione (0.5 g, 1.9 mmol) and potassium carbonate (1.04 g, 7.5 mmol) in tetrahydrofuran. The reaction mixture is stirred at room temperature for 16 hours, heated at reflux for 90 hours, filtered through diatomaceous earth and concentrated in vacuo to obtain a residue. Flash column chromatography of the residue using silica gel and 33% to 50% ethyl acetate in hexanes solutions gives the title product as a clear oil (0.63 g) which is identified by $^1$HNMR spectral analysis.

EXAMPLE 13

Preparation of 9-chloro-4-tert-butyl-3,4-dihydro-7-methyl-1H-1,4-benzodiazepine-2,5-dione

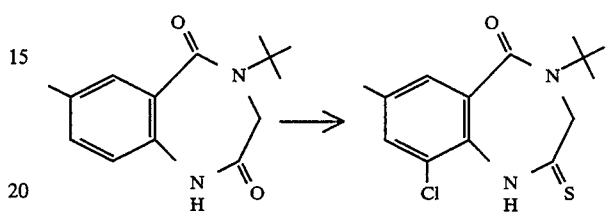

Chlorine gas (100 mL, 4.1 mmol) is added via syringe to a mixture of 4-tert-butyl-3,4-dihydro-7-methyl-1H-1,4-benzodiazepine-2,5-dione (1.0 g, 4.1 mmol) and a few grains of ferric chloride hexahydrate in acetic acid. The reaction mixture is stirred at room temperature overnight, poured into water and extracted with ethyl acetate. The combined organic extracts are washed sequentially with water, dilute sodium hydrogen carbonate solution and brine, dried over anhydrous magnesium sulfate and concentrated in vacuo to obtain a foam. Flash column chromatography of the foam using silica gel and a 20:1 methylene chloride/ethyl acetate solution gives the title product as a white solid (0.5 g, mp 151°–152° C.).

What is claimed is:

1. A method for controlling undesirable plant species which comprises applying to the foliage of said plants or to the soil or water containing seeds or other propagating organs thereof, a herbicidally effective amount of a compound having the structural formula

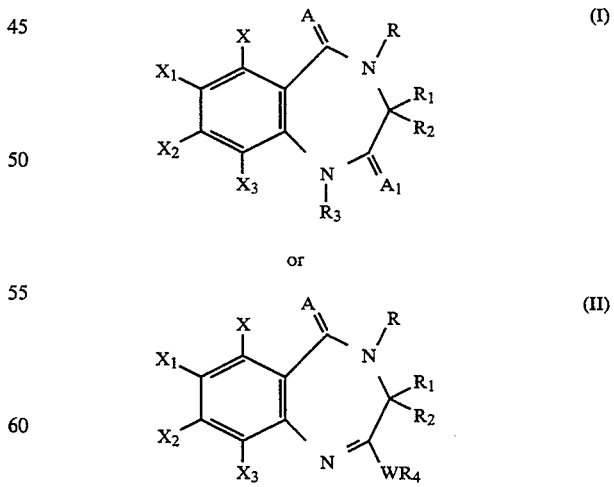

wherein

X is hydrogen, halogen, $C_1$–$C_4$haloalkyl, $C_1$–$C_4$alkoxy, $C_1$–$C_4$haloalkoxy, $C_2$–$C_3$alkenyl, $C_2$–$C_4$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$X_1$ is hydrogen, halogen, methyl, $C_1$–$C_4$haloalkyl, $C_1$–$C_4$alkoxy, $C_1$–$C_4$haloalkoxy, $C_2$–$C_5$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$X_2$ is hydrogen, $C_1$–$C_4$alkyl, $C_1$–$C_4$alkoxy, $C_1$–$C_4$haloalkoxy, $C_2$–$C_3$alkenyl, $C_2$–$C_3$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$X_3$ is hydrogen, $C_1$–$C_4$alkyl, $C_1$–$C_4$haloalkyl, $C_1$–$C_4$haloalkoxy, $C_2$–$C_3$alkenyl, $C_2$–$C_3$alkynyl, $CO_2R_5$, $C(O)NR_6R_7$, $S(O)_mR_8$, $C(O)R_9$, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_5$ is hydrogen, $C_1$–$C_4$alkyl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or an alkali metal, alkaline earth metal, manganese, copper, zinc, cobalt, silver, nickel, ammonium or organic ammonium cation;

$R_6$ and $R_7$ are each independently $C_1$–$C_4$alkyl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or $R_6$ and $R_7$ are taken together to form a ring in which $R_6R_7$ is represented by —$(CH_2)_n$— where n is an integer of 2, 3, 4 or 5;

m is an integer of 0, 1 or 2;

$R_8$ is hydrogen, $C_1$–$C_4$alkyl, $C_1$–$C_4$haloalkyl, $NR_{10}R_{11}$, $OR_{12}$ or phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_{10}$ and $R_{11}$ are each independently hydrogen, $C_1$–$C_4$alkyl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or $R_{10}$ and $R_{11}$ are taken together to form a ring in which $R_{10}R_{11}$ is represented by —$(CH_2)_q$— where q is an integer of 2, 3, 4 or 5;

$R_{12}$ is hydrogen or $C_1$–$C_4$alkyl;

$R_9$ is hydrogen, $C_1$–$C_4$alkyl or phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

A, $A_1$ and W are each independently O or S with the proviso that when $A_1$ is S then A is O;

R is $C_3$–$C_6$cycloalkyl, $C_2$–$C_5$alkenyl, $C_2$–$C_5$alkynyl, $C_1$–$C_5$alkyl optionally substituted with one $CO_2R_{13}$ group, one phenyl group optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or one 5- or 6-membered heterocycle group containing one to three nitrogen atoms, one oxygen atom and/or one sulfur atom and two to five carbon atoms optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups with the proviso that the para-position of the phenyl ring is not substituted, a 5- or 6-membered heterocycle group containing one to three nitrogen atoms, one oxygen atom and/or one sulfur atom and two to five carbon atoms optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or R may be taken together with $R_1$ and the atoms to which they are attached to form a five membered saturated ring substituted with one to three $C_1$–$C_4$alkyl groups;

$R_{13}$ is hydrogen, $C_1$–$C_4$alkyl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or an alkali metal, alkaline earth metal, manganese, copper, zinc, cobalt, silver, nickel, ammonium or organic ammonium cation;

$R_1$ and $R_2$ are each independently hydrogen, methyl, ethyl, or $R_1$ may be taken together with R and the atoms to which they are attached to form a five membered saturated ring substituted with one to three $C_1$–$C_4$alkyl groups, and when taken together, $R_1$ and $R_2$ may form a ring in which $R_1R_2$ is represented by —$(CH_2)_t$— where t is an integer of 2, 3, 4, 5 or 6 with the proviso that when $R_1$ is methyl or ethyl then $R_2$ is hydrogen;

$R_3$ is hydrogen, $C_1$–$C_4$alkyl or hydroxy with the proviso that when $R_3$ is hydroxy, $X_2$ is other than $C_1$–$C_4$alkyl, and further with the proviso that when $R_3$ is $C_1$–$C_4$alkyl, $X_1$ is other than hydrogen or methyl; and $R_4$ is $C_1$–$C_6$alkyl, $C_3$–$C_6$cycloalkyl, $C_1$–$C_6$haloalkyl, $C_2$–$C_6$alkenyl, $C_2$–$C_6$alkynyl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or phenyl optionally substituted with one halogen, nitro, cyano, $C_1$–$C_4$alkyl, $C_1$–$C_4$haloalkyl, $C_1$–$C_4$alkoxy or $C_1$–$C_4$haloalkoxy group;

and the optical isomers and diastereomers thereof;

and mixtures thereof.

2. The method according to claim 1 wherein

X and $X_2$ are hydrogen;

$X_1$ is hydrogen, halogen, methyl, $C_1$–$C_4$alkoxy or $C_2$–$C_3$alkynyl;

$X_3$ is hydrogen or methyl;

A is O;

$A_1$ and W are each independently O or S;

R is $C_3$–$C_6$cycloalkyl, $C_1$–$C_5$alkyl, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups with the proviso that the para-position of the phenyl ring is not substituted, or R may be taken together with $R_1$ and the atoms to which they are attached to form a five membered saturated ring substituted with one to three $C_1$–$C_4$alkyl groups;

$R_1$ and $R_2$ are hydrogen or $R_1$ may be taken together with R and the atoms to which they are attached to form a five membered saturated ring substituted with one to three $C_1$–$C_4$alkyl groups;

$R_3$ is hydrogen or hydroxy; and $R_4$ is $C_1$-$C_6$alkyl, $C_3$-$C_6$cycloalkyl, $C_1$-$C_6$haloalkyl, $C_2$-$C_6$alkenyl, $C_2$-$C_6$alkynyl, benzyl optionally substituted with one or more halogen, nitro, cyano, $C_1$-$C_4$alkyl, $C_1$-$C_4$haloalkyl, $C_1$-$C_4$alkoxy or $C_1$-$C_4$haloalkoxy groups, or phenyl optionally substituted with one halogen, nitro, cyano, $C_1$-$C_4$alkyl, $C_1$-$C_4$haloalkyl, $C_1$-$C_4$alkoxy or $C_1$-$C_4$haloalkoxy group.

3. The method according to claim 2 wherein
X, $X_2$, $X_3$, $R_2$ and $R_3$ are hydrogen;
$X_1$ is hydrogen, halogen or methyl;
A, $A_1$ and W are O;
R is $C_3$-$C_6$cycloalkyl, $C_1$-$C_5$alkyl, or R may be taken together with $R_1$ and the atoms to which they are attached to form a five membered saturated ring substituted with one to three $C_1$-$C_4$alkyl groups;
$R_1$ is hydrogen or $R_1$ may be taken together with R and the atoms to which they are attached to form a five membered saturated ring substituted with one to three $C_1$-$C_4$alkyl groups; and
$R_4$ is $C_1$-$C_6$alkyl.

4. The method according to claim 3 wherein the compound is selected from the group consisting of
7-chloro-4-tert-butyl-3,4-dihydro-1H-1,4-benzodiazepine-2,5-dione;
7-chloro-1,2,3,11a-tetrahydro-3,3-dimethyl-5H-pyrrolo-[2,1-c][1,4]benzodiazepine-5,11(10H)-dione;
7-chloro-1,2,3,11a-tetrahydro-2,3,3-trimethyl-5H-pyrrolo[2,1-c][1,4]benzodiazepine-5,11(10H)-dione;
4-tert-butyl-3,4-dihydro-7-methyl-1H-1,4-benzodiazepine-2,5-dione;
7-chloro-3,4-dihydro-4-(2,2-dimethylpropyl)-1H-1,4-benzodiazepine-2,5-dione;
1,2,3,11a-tetrahydro-3,3,7-trimethyl-5H-pyrrolo-[2,1-c][1,4]benzodiazepine-5,11(10H)-dione;
7-bromo-4-tert-butyl-3,4-dihydro-1H-1,4-benzodiazepine-2,5-dione;
4-tert-butyl-3,4-dihydro-7,9-dimethyl-1H-1,4-benzodiazepine-2,5-dione;
4-tert-butyl-7-chloro-3,4-dihydro-2-thio-1H-1,4-benzodiazepine-2,5-dione;
4-tert-butyl-7-chloro-3,4-dihydro-9-methyl-1H-1,4-benzodiazepine-2,5-dione; and
4-tert-butyl-7-chloro-3,4-dihydro-2-methoxy-5H-1,4-benzodiazepin-5-one.

5. The method according to claim 1 which comprises applying said compound to the soil, water, or other medium containing seeds or other propagating organs of said plants at a rate of about 0.10 kg/ha to 10.0 kg/ha.

6. A method for the selective control of undesirable plant species in the presence of cereal crops which comprises applying to the foliage and stems of the crops and undesirable plant species growing in the presence thereof or to the soil or water containing seeds or other propagating organs of the undesirable plant species in which the crops are growing, an amount of a compound having the structural formula

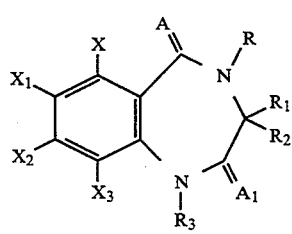
(I)

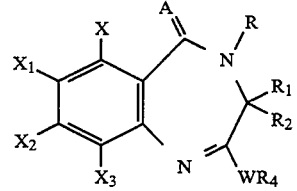
(II)

wherein X, $X_1$, $X_2$, $X_3$, A, $A_1$, W, R, $R_1$, $R_2$, $R_3$ and $R_4$ are as described in claim 1, effective for the selective control of the undesirable plant species growing in the presence of the crops.

7. The method according to claim 6 wherein X, $X_1$, $X_2$, $X_3$, A, $A_1$, W, R, $R_1$, $R_2$, $R_3$ and $R_4$ are as described in claim 2.

8. The method according to claim 7 wherein X, $X_1$, $X_2$, $X_3$, A, $A_1$, W, R, $R_1$, $R_2$, $R_3$ and $R_4$ are as described in claim 3.

9. The method according to claim 8 wherein the compound is selected from the group consisting of 7-chloro-4-tert-butyl-3,4-dihydro-1H-1,4-benzodiazepine-2,5-dione, and
7-chloro-1,2,3,11a-tetrahydro-3,3-dimethyl-5H-pyrrolo-[2,1-c][1,4]benzodiazepine-5,11(10H)-dione.

10. The method according to claim 6 wherein the cereal crops are selected from the group consisting of corn, barley, wheat, oat, rye and rice.

11. The method according to claim 10 wherein the cereal crop is corn.

12. The method according to claim 6 wherein the compound is applied to the crops and undesirable plant species or to the soil or water containing seeds or other propagating organs of the undesirable plant species at a rate of about 0.10 kg/ha to 2.5 kg/ha.

13. A herbicidal composition which comprises an agronomically acceptable carrier and a herbicidally effective amount of a compound having the structural formula

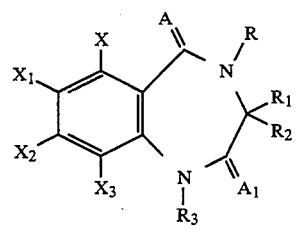
(I)

or

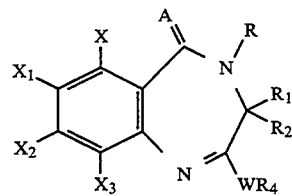
(II)

wherein X, X1, X2, $X_3$, A, $A_1$, W, R, $R_1$, $R_2$, $R_3$ and $R_4$ are as described in claim 1.

14. The composition according to claim 13 wherein X, $X_1$, $X_2$, $X_3$, A, $A_1$, W, R, $R_1$, $R_2$, $R_3$ and $R_4$ are as described in claim 2.

15. The composition according to claim 14 wherein X, $X_1$, $X_2$, $X_3$, A, $A_1$, W, R, $R_1$, $R_2$, $R_3$ and $R_4$ are as described in claim 3.

* * * * *